(12) United States Patent
Rossi

(10) Patent No.: US 6,323,230 B1
(45) Date of Patent: Nov. 27, 2001

(54) USE OF NITROGEN HETEROCYCLIC AROMATIC DERIVATIVES IN THE TOPICAL TREATMENT OF THE EPITHELIAL TISSUES DISEASES

(75) Inventor: Carla Rossi, Milan (IT)

(73) Assignee: Geange Ltd., Dublin (IE)

( * ) Notice: Subject to any disclaimer, the term of this patent is extended or adjusted under 35 U.S.C. 154(b) by 0 days.

(21) Appl. No.: 09/445,219
(22) PCT Filed: Jun. 4, 1998
(86) PCT No.: PCT/EP98/03497
§ 371 Date: Apr. 24, 2000
§ 102(e) Date: Apr. 24, 2000
(87) PCT Pub. No.: WO98/55118
PCT Pub. Date: Dec. 10, 1998

(30) Foreign Application Priority Data

Jun. 5, 1997 (IT) ................................. MI97A1329

(51) Int. Cl.$^7$ .................. C07D 249/10; A61K 31/41; A61P 17/06
(52) U.S. Cl. .................. 514/381; 514/383; 514/384; 548/250; 548/251; 548/253; 548/254; 548/262.2; 548/264.6
(58) Field of Search .................. 514/381, 383, 514/384; 548/250, 251, 253, 254, 262.2, 264.6, 263.2

(56) References Cited

U.S. PATENT DOCUMENTS

| 4,379,155 | 4/1983 | Omodei-Sale et al. ............... 424/269 |
| 4,535,090 | * 8/1985 | Galliani et al. ...................... 514/383 |

FOREIGN PATENT DOCUMENTS

| 28 19 372 A1 | * 11/1978 | (DE) . |
| 29 43 326 A | 5/1980 | (DE) . |
| 43 20 801 | 1/1995 | (DE) . |
| 0 080 053 A | 6/1983 | (EP) . |
| 0 01 1129 A | 5/1988 | (EP) . |
| 95/13268 | * 11/1978 | (WO) . |
| WO 94 17068 | 8/1994 | (WO) . |

OTHER PUBLICATIONS

Mistrello et al Immunological Profile of DL111–IT Immunopharmacology vol. 10, 1985, pp 163–169 XP002082252.
De Gruyter Psychyrembel Klinisches Wörterbuch 1994 XP002082253 p. 142.

* cited by examiner

Primary Examiner—Floyd D. Higel
Assistant Examiner—Andrea M D'Souza
(74) Attorney, Agent, or Firm—Nixon & Vanderhye

(57) ABSTRACT

Derivatives of general chemical formula L(I) and (IV)

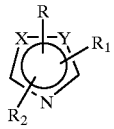

(I)

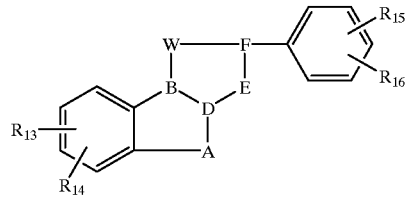

(IV)

are used in the topical treatment of diseases of the epithelial tissues, like psoriasis (epidermis) and ulcerative colitis L(lower intestine). These compounds display a high efficacy when administered for example by epicuaneous route in the case of dermatological illnesses like psoriasis, atopic dermatitis and other similar affections, or when administered by oral or rectal route in the case of diseases of the epithelia of the lower intestine like the ulcerative colitis and Crohn's disease.

29 Claims, No Drawings

USE OF NITROGEN HETEROCYCLIC AROMATIC DERIVATIVES IN THE TOPICAL TREATMENT OF THE EPITHELIAL TISSUES DISEASES

This application is a 371 of PCT/EP98/03497 filed Jun. 4, 1998.

OBJECT OF THE PRESENT INVENTION

Objects of the present invention is the use of nitrogen heterocyclic aromatic derivatives in the topical treatment of the diseases of the epithelial tissues.

Object of the present invention is also a chemical class of nitrogen heterocyclic aromatic derivatives and a procedure for their preparation.

Object of the present invention are pharmaceutical preparations which contains, as active principle, heterocyclic aromatic derivatives and their use in the topical treatment of the diseases of the epithelial tissues.

STATUS OF THE TECHNIQUE

Among all the diseases of the epithelial tissues, (epidermis, intestinal and bronchi mucosae), some of the more studied, because they large diffusion, are surely the psoriasis (epidermis) and the ulcerous cholitis (low intestine).

The psoriasis is a skin disease of genetic origin (phenotypes HLA with HLA-cw6 antigen) multi-factorial, characterised by inflammation and hyper-plasia of the epidermis with consequent plaques formation. In the psoriasis lesions, the rate of cell proliferation is of at least 10 times higher than normal. Different hypotheses exist on the origin of dermatological diseases like psoriasis; one of this suggests that a primary defect in keratinocyte growth regulation in the germinative stratum, may lead to epidermis hyper-proliferation. This hypothesis has been recently supported by finding showing the involvement of cytokines (interleukin, interferon, growth factors including EGF) in its pathogenesis.

The anti-proliferative and inflammatory components of psoriasis need for a therapeutic approach which can affect both or at least one of the two mechanisms; from a practical viewpoint, depending on the severity of the pathology, the pharmacological and/or physical treatment is strengthen while the therapeutic index is reduced and the untoward effects increased.

It is a fact that, by increasing the severity and recrudescence of the disease, the therapies at present considered more effective and of large use start with topical treatments by emollients and keratolytic, then with tars, topical corticosteroids, antralins, antimicrobics, UVB applications combined with Goeckmen Ingram, photochemio therapy PUVA, until to use systemic treatments like oral corticosteroids, retinoids, metotrexate, hydroxyurea, cyclosporine.

When both topical pharmacological and physical therapies, including the use of PUVA (induction of the covalent binding of psoralens with the pyrimidinic bases of DNA) result ineffective, the systemic therapies remain the only available. These are however performed by utilising drugs of high general toxicity but not always effective, like corticosteroids, retinoids, chemotherapics and cyclosporine.

When the therapeutic index is considered the results obtained are often poor whereas the recrudescence, of the illness is rapid.

Therefore, the compounds nowadays used in the therapy of psoriasis are scarcely effective and produce several and severe side-effects.

Similarly, about 20% of all the inflammatory diseases of the low intestine including the Crohn illness, do not improve by the most commonly used anti-inflammatory therapies with 5-amino-salycilic acid and cortico-steroids, while need of more aggressive treatments with immuno-suppressants. Among these latter, azathiopirine and methotrexate are used, in spite of their cytotoxic activity leading in the course of prolonged therapeutic cycles to serious adverse events as pancreatitis, bone marrow depression, hepatitis and allergic reactions.

Therefore, the availability of non-cytotoxic drugs, endowed with a high anti-proliferative activity attained locally on the epithelia of the intestinal mucosae, is to be regarded as an useful progress in the therapy of severe diseases of the low intestine.

OBJECTIVES OF THE INVENTION

Objective of the present invention is to make available nitrogen heterocyclic aromatic derivatives to be used in the topical pharmacological treatment of diseases of epithelial tissues..

Objective of the present invention is also to make. available nitrogen heterocyclic aromatic derivatives displaying their activity when topically administered by epicutaneous, oral or rectal route.

Objective of the present invention is also to make available pharmaceutical formulations, containing at least one nitrogen heterocyclic aromatic derivative as active principle, to be used in the treatment of diseases of the epithelial tissues, that display their activity when administered epicutaneously in the dermatological affections and by oral or rectal route in the diseases of the low intestine, that are well tolerated and able to allow a high therapeutic index.

Objective of the present invention is also to make available nitrogen heterocyclic aromatic derivatives to be used in the treatment of diseases of the epithelial tissues and displaying a high activity when administered topically, thus able to reduce the risk of systemic side-effects.

Objective of the present invention is also to make available nitrogen heterocyclic aromatic derivatives to be used in the treatment of diseases of the epithelial tissues in combination with other compounds also employed in the same therapeutic areas in order to achieve synergistic effects.

DESCRIPTION OF THE INVENTION

These and other objectives with further advantages which are clarified in the description below, are obtained by the nitrogen heterocyclic aromatic derivatives having the following general formula:

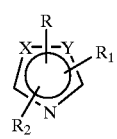

(I)

where when $X=Y$, $X, Y=N$;

when $X=Y$, $X, Y=N, C, CH$;

R is chosen between:

hydrogen;
any group able to form a bond with a nitrogen atom,
- —$COR_8$ where $R_8$ is $C_1$–$C_4$ alkyl, $C_2$–$C_4$ alkenyl, $C_2$–$C_4$ alkinyl, phenyl possibly substituted by 1 to 3 substituents, benzyl, $C_1$–$C_4$ alkylamino, di-($C_1$–$C_4$ alkyl)amino, phenylamino possibly substituted by 1 to 3 substituents, $C_1$–$C_4$ halolkyl, $C_1$–$C_4$ alkoxy, benzyloxy. Each eventual substituent being independently chosen among: halogen, $C_1$–$C_4$ alkyl, $C_1$–$C_4$ alkoxy, trifluoro-methyl, CN, nitro, amino, di-($C_1$–$C_4$ alkyl)amino, acylamino$C_2$–$C_4$ and methylendioxy;
- $SO_2R_{12}$, where $R_{12}$ is chosen among: $C_1$–$C_4$ alkyl, phenyl, ($C_1$–$C_4$ alkyl)phenyl, ($C_1$–$C_4$ alkoxy)phenyl, acetylphenyl $R_1$ has the following general formula:

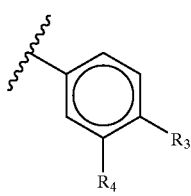

(II)

where
$R_3$ and $R_4$ are independently chosen among:
  hydrogen,
  halogen,
  $C_1$–$C_{10}$ alkyl or alkoxyl $C_1$–$C_{10}$,
  allyloxy, propergyloxy,
  trifluoro-methyl,
  phenyl,
  di-methylamino,
or
$R_3$ and $R_4$ together form a methylendioxy group;
$R_2$ has the following general structure:

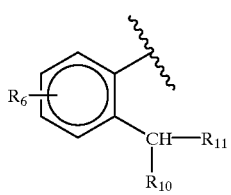

(III)

where
$R_6$ is chosen among:
  hydrogen,
  halogen,
  $C_1$–$C_{10}$ alkyl or alkoxyl $C_1$–$C_{10}$;
where
$R_{10}$ is chosen among:
  hydrogen,
  methyl;
where
$R_{11}$ is chosen among:
  hydrogen,
  $C_1$–$C_4$ alkyl,
  formyl,
$OR_5$, where $R_5$ is chosen among hydrogen, $C_1$–$C_4$ alkyl, $SO_2R_{11}$, where $R_{11}$ is defined as above, or $R_5$ is chosen among:

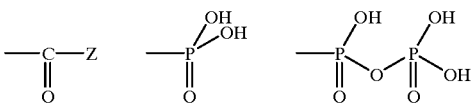

where $Z=OR_7$ with $R_7$ is chosen among a saturated or non-saturated, linear or branched $C_1$–$C_{20}$ aliphatic hydrocarbon, or is chosen according to the following formula:

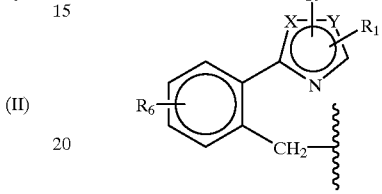

(XII)

where R, $R_1$, $R_6$, X and Y are defined as above or Z is chosen among $C_1$–$C_{20}$ linear or branched alkyl, $C_2$–$C_4$ alkenyl, $C_2$–$C_4$ alkinyl, phenyl possibly substituted by 1 to 3 substituents, benzyl, $C_1$–$C_4$ alkylamino, di-($C_1$–$C_4$ alkyl)amino, phenyl-amino possibly substituted by 1 to 3 substituents, $C_1$–$C_4$ halo-alkyl, $C_1$–$C_4$ alkoxy, benzyloxy. Each eventual substituent being independently chosen among: halogen, $C_1$–$C_4$ alkyl, $C_1$–$C_4$ alkoxy, trifluoro-methyl, CN, nitro, amino, di-($C_1$–$C_4$ alkyl)amino, acylamino$C_2$–$C_4$ and methylendioxy;
or Z is chosen equal to $NHR_9$ where $R_9$ is a linear or branched $C_1$–$C_{20}$ alkyl chain, or mentioned $R_{10}$ and $R_{11}$, together form a further bond between the carbon atom and one oxygen atom;
mentioned $R_1$ and $R_2$ are never located on two adjacent atoms of the heterocyclic aromatic ring;
or by nitrogen heterocyclic aromatic derivatives of general formula as follows:

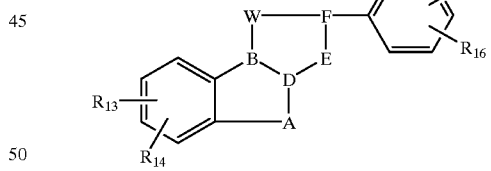

(IV)

where:
$R_{15}$ and $R_{16}$ are chosen among:
  hydrogen,
  phenyl,
  hydroxy,
  $C_1$–$C_4$ alkyl,
  $C_1$–$C_4$ alkoxy,
  $C_3$–$C_5$ alkenyloxy,
  $C_3$–$C_5$ alkenyloxy,
  $C_3$–$C_6$ cyclo-alkyloxy,
  benzyloxy,
  halogens,
or
$R_{15}$ and $R_{16}$ together form a methylendioxy group;
$R_{13}$ and $R_{14}$ are chosen among:

hydrogen,
halogens,
$C_1$–$C_4$ alkoxy;

A is chosen as:
—$CH_2$—, —CH=CH—, —$CH_2$—$CH_2$—, —$(CH_2)_3$, —$CH_2$—S—;

B is chosen as: C, N;

D is chosen as: C, N;

or B and D together are equal to —C=C—;

E is chosen as: N, C, CO, NH, CH, $NR_{17}$, $CR_{17}$ where $R_{17}$ is chosen as a linear $C_1$–$C_4$ alkyl;

F is chosen as: CH, N;

W is chosen as: N, NH, CH, $NR_{17}$, $CR_{17}$, $CR_{18}$, where $CR_{17}$ is defined as above and $R_{18}$ is chosen as carboxy, carbo($C_1$–$C_4$ alkyl), carbamyl, mono or di-($C_1$–$C_4$ alkyl)carbamyl, hydroxymethyl;

The mentioned derivatives of general formulas (I) and (IV) being used in the topical pharmacological treatment of diseases of epithelial tissues.

According to the present invention, the term saturated or non-saturated aliphatic hydrocarbon means a linear or branched alkyl, alkenyl or alkinyl chain which contains one or more double or triple bonds. Always according to the present invention, the term alkyl or alkoxyl means a linear or branched alkyl or alkoxyl group.

Namely, the mentioned nitrogen heterocyclic aromatic derivative of formula (I) is a derivative of pyrazole, imidazole and 1H-1,2,4-triazole respectively:

  

Of particular interest are those derivatives of formula (IV) where:

$R_{13}$ and $R_{14}$ is hydrogen, A is chosen among —$CH_2$—, —CH=CH—, —$CH_2$—$CH_2$—; D is chosen as N, B is chosen equal to C, W is chosen as N, $R_{15}$ is hydrogen, and $R_{16}$ is chosen between $C_1$–$C_4$ alkoxy and phenyl.

Derivatives of general chemical formula (I) and (IV) according to the present invention are advantageously used in the topic treatment of the diseases of the epithelial tissues, like the psoriasis and atopic dermatitis (epidermis) and the ulcerous cholitis (low intestine) or when administered by oral or for example by rectal route in the case of diseases of the epithelia of the low intestine like the ulcerous cholitis and the Crohn illness Namely, according to the present invention, of particular interest were those derivatives having formulas derived from general structures (I) and (IV), as follows:

(X)

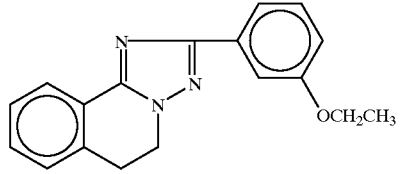

(XI)

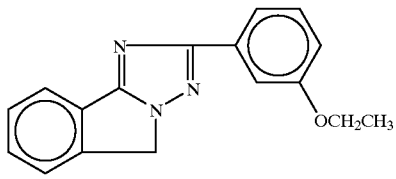

(XII)

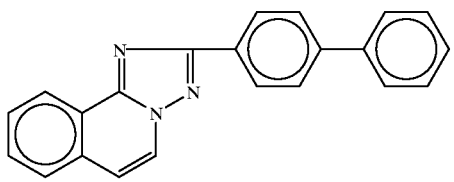

(XIII)

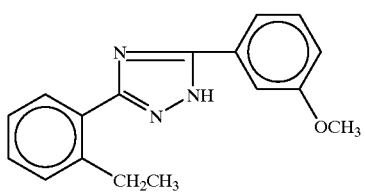

(V)

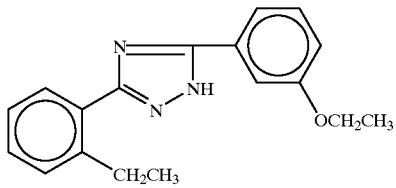

(VI)

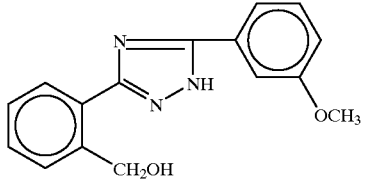

(VII)

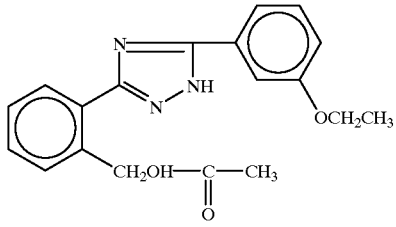

(VIII)

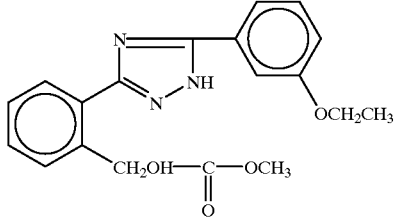

-continued (IX)

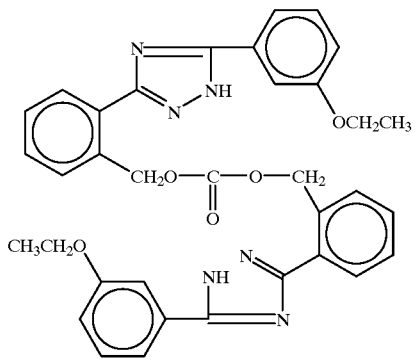

(XIV)

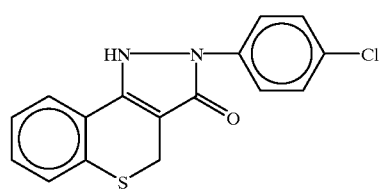

According to the present invention, of particular interest were derivatives of formula (I) where:

when X=Y, X,Y=N;

when X≠Y, X,Y=N, C, CH;

R is chosen among:
hydrogen, any group able to form a bond with a nitrogen atom, —$COR_8$ where $R_8$ is a saturated or non-saturated $C_1$–$C_{10}$ aliphatic hydrocarbon;

$R_1$ has the following general structure:

(II)

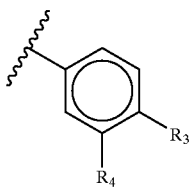

where:

$R_3$ and $R_4$ are selected among
hydrogen,
halogen,
$C_1$–$C_{10}$ alkyl or alkoxyl $C_1$–$C_{10}$, or $R_3$ and $R_4$ together form a methylendioxy group;

$R_2$ has the following general structure:

(III)

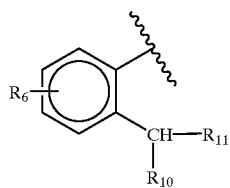

where
$R_6$ is chosen among:
hydrogen,
halogen,
$C_1$–$C_{10}$ alkyl or $C_1$–$C_{10}$ alkoxyl;
where
$R_{10}$ is chosen as hydrogen,
where
$R_{11}$ is chosen as: $OR_5$, where $R_5$ is chosen among $C_1$–$C_{20}$ saturated or non-saturated, linear or branched aliphatic hydrocarbon, or $R_5$ is chosen among:

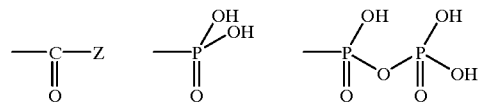

where Z=$OR_7$ with $R_7$ chosen among a saturated or non-saturated, linear or branched $C_1$–$C_{20}$ aliphatic hydrocarbon, or is chosen according to the following formula:

(XII)

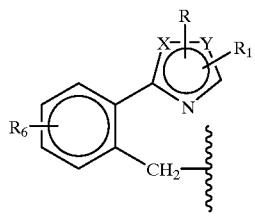

where R, $R_1$, $R_6$, X and Y are defined as above or Z is chosen equal to $NHR_9$ where $R_9$ is a $C_1$–$C_{20}$ linear or branched alkyl chain.

Mentioned $R_1$ and $R_2$ being never located on two adjacent atoms of the heterocyclic aromatic ring.

The derivatives of the present invention, when administered topically by epicutaneous, oral route, at doses much lower than those toxic or able to induce not desired side-effects, were shown to be highly effective in those therapies used to treat dermatological illnesses as for example the psoriasis and the atopic dermatitis as well as in the therapy of diseases of the epithelial mucosae of the low intestine.

The derivatives of the present invention displayed a high efficacy when administered by topical routes, thus their use in the treatment of skin diseases and of the intestinal mucosae, and namely in the therapy of psoriasis or of the ulcerous cholitis, allows to markedly reduce the risk of systemic untoward effects.

Apropos it has to be outlined as some of the compounds of the present invention when tested as anti-fertility agents display by oral route an activity much lower than that observed after parenteral injection, see Galliani et al., J.Pharm.Dyn. 5, 55–61 (1982). This finding, however, rather than to a low absorption is related to a rapid and extensive hepatic first-pass effect leading to the formation of inactive metabolites, see Assandri et al., Reviews on Drug Met, & Drug Interactions, IV, 237–261 (1982); A.Assandri et al., Xenobiotica 14, 429–443 (1984). This behaviour, due to the limitation of systemic toxic effects, becomes useful in the topical treatment of both dermatological and intestinal diseases. In addition since the derivatives of the present invention display their activity through a mechanism, not yet clarified, but very likely different from that of other drugs currently used in the therapy of psoriasis and of the ulcerous cholitis, they can be advantageously used in combination so to give rise to synergistic responses.

Of particular interest, due to its high efficacy, is compound (XIII), which, for example, can be synthesised according to the following scheme:

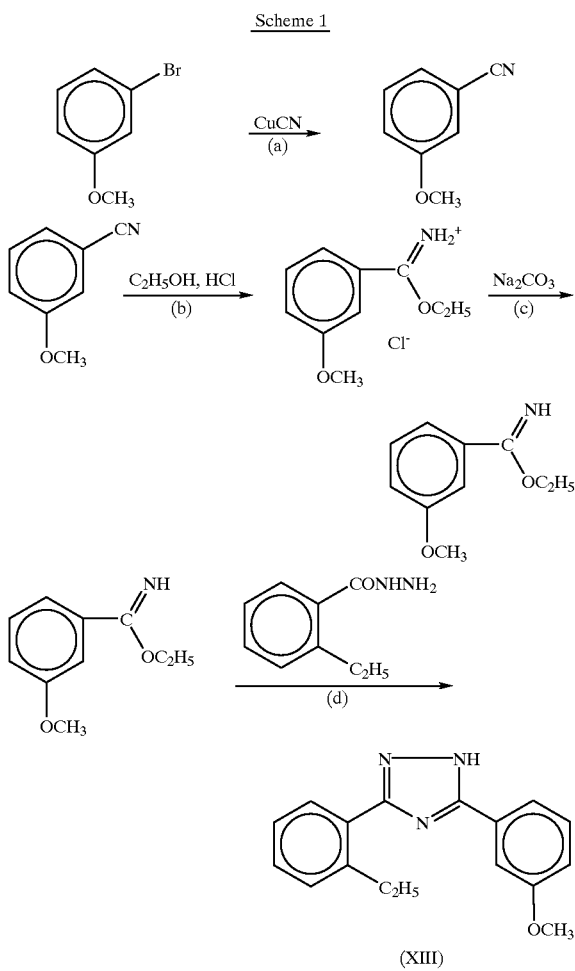

EXAMPLE 1
(a) 3-METHOXY BENZONITRILE 3-bromoanysole (210 mg, 1.12 mmoles) and CuCN (93.14 mg, 1.04 mmoles) were dissolved in N-methyl pyrrolidone (mL) and the reaction mixture is warmed to 220° C. for 2 hours. After cooling to 50° C., the reaction mixture was added both 6 mL of an aqueous solution containing 400 mg of $FeCl_3.6H_2O$ and 0.6 mL 37% HCl, then was maintained under stirring at 65° C. for 20 min. After addition of 20 mL water the raw product was extracted by ethyl ether (5×20 mL); the organic phase de-hydrated by $Na_2SO_4$, was dried giving 114.3 mg of the crude compound (93.4%)

(b), (c) ETHYL ETHER OF THE 3-METHOXYBENZOIMIDIC ACID

Crude 3-Methoxy benzonitrile (114.3 mg) dissolved into anhydrous ethyl ether (3 mL) and anhydrous ethanol (0.15 mL), was cooled to 4° C.; anhydrous HCl is then bubbled for 7 hours. After one night at 4° C., the intermediate precipitate (hydrochloride salt) was taken up with 8% $Na_2CO_3$ in water (4 mL) and extracted with ethyl ether (5×10 mL). $Na_2SO_4$ was added to the organic phase, and after filtration the solution was evaporated to dryness to give 85 mg of immino ether (44.65%).

(d) 3-(2-ETHYLPHENYL)-5-(3-METHOXYPHENYL)-1h-1,2,4 TRIAZOLE (XIII)

A mixture of immino ether (85 mg, 0.474 mmoles) and 2-ethyl benzo-hydrazide (164 mg, 1 mmole) in acetonitrile (0.5 mL), was warmed under reflux. After 1 hour stirring, solvent was distilled and substituted by 2-ethoxyethanol (0.6 mL). The reaction mixture was refluxed for 3 hours, the solvent evaporated under vacuum and the residue, re-dissolved in $CH_2Cl_2$ (2 mL), was chromatographed on a silica gel column (10 g). As elution solvents, mixtures of $CH_2Cl_2$ and $CH_3COOC_2H_5$ in varying proportion (99:1 to 95:5) were used. Fractions containing the desired product were collected, solvent evaporated to give 96,27 mg (72.6%) of compound (XIII). Of particular interest, was compound (XIV), which, can be synthesised according to the procedure hereafter reported in example 2.

EXAMPLE 2

A mixture containing 60 g (0.270 moles) of 3-carbomethoxy-4-thio-cromanone (T. Moriwake, J:Med. Chem. 9, 163 (1966), 42.4 g (o,297 moles) of p-chlorphenyl-hydrazine and 18 mL of acetic acid, was warmed in an oil bath, under nitrogen atmosphere at 115° C. for 30 min. The resulting solid yellow precipitate was heated further at 180° C. for 1.5 hours, then cooled and the excess of acetic acid eliminated under vacuum. The semi-solid residue was repeatedly disintegrated into large ether volumes while each time the suspension was filtered. The crude product (71 g) was dissolved in 3 L of iso-propanol, concentrated to 1% L and cooled to give 54 g (64%) of compound (XIV).

Melting point: 235–237° C.

IR 3.65 (br, NH), 6.12, 6.26, 7.63, 9.23, 12.1 nm.

MS: m/e 314 (calculated 314)

NMR (DMSO $d_6$): τ6.0 (S, 2H, $CH_2$), 2.1–2.8 (m, 8H, aromatic protons).

The derivatives object of the present invention are, for example, advantageously prepared starting from a derivative (XV) with the following chemical formula:

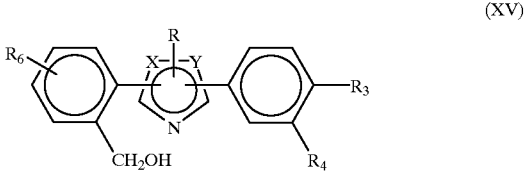

(XV)

More particularly, when substituents $R_1$ and $R_2$ are in position 3 and respectively, the corresponding derivative (XI) has the following chemical formula:

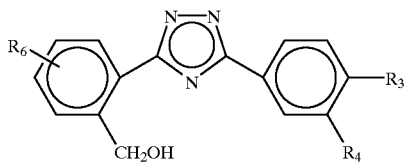

(XVI)

The above mentioned derivative of formula (XVI), is prepared according to different procedures already reported by the literature and is described in EP11129. In this case the method consists in the rearrangement of hydrazones of substituted benzaldehydes with 4-hydrazino-1H-2,3-benzoxazines of formula (X)

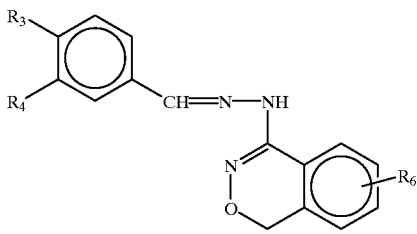

(XVII)

wherein $R_3$, $R_4$ and $R_6$ are as defined as for the derivatives of formula (I).

This rearrangement simply occurs by refluxing the hydrazone III in a high boiling inert organic solvent, such as for instance, xylene, N,N-dimethylformamide, and halogenated aromatic hydrocarbons, for about 30 minutes and then recovering the compound II by filtration.

Another suitable method for the preparation of the 2-hydroxymethyl-phenyl derivatives of formula (XVI), consists in the oxidation of the corresponding 2-methylphenyl triazoles, either directly to the alcohol (XVI) or to the corresponding carboxylic acid followed by a reduction of this latter to the alcohol(XVI).

In the former case, ceric ammonium nitrate or silver (II)oxide are the oxidising agents which may be suitably employed, while in the latter, the oxidative step is carried out with any of the several oxidisers known in the art to transform a methyl group on an aromatic ring to a carboxylic group, such as permanganate, nitric acid, and dichromate, and the reductive step in easily performed with a metal hydride.

Alternatively, the starting compound of formula (XVI) can be prepared by following the process described in EP80053.

Also derivative (XVI) where $R_6$ and $R_3$ are hydrogens and $R_4$ is equal to $OCH_2CH_3$, is prepared according to example 9 as reported below.

Referring to compounds of formula (I), object of the present invention, the procedure for their preparation starting from the corresponding derivative of formula (XV) varies depending whether the substituent R is hydrogen or a group $R_8$—CO wherein $R_8$ has the same meaning as above in relation to derivatives of formula (I).

When R is hydrogen, the derivative of formula (XV) is prepared according to different procedures already reported by the literature, in equimolar ratio with phosgene ($COCl_2$) and the resulting chloro-carbonate is left to react with a derivative Z where Z=$OR_7$ and $R_7$ is chosen among a saturated or non-saturated, linear or branched aliphatic hydrocarbon $C_1$–$C_{20}$, or is chosen according to the following formula:

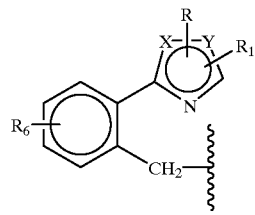

(XII)

where R, $R_1$, $R_6$, X and Y are defined as above, or Z is chosen equal to NH-$R_9$ where $R_9$ is a linear or branched $C_1$–$C_{20}$ alkyl chain.

The derivative of formula (I) where R is chosen as hydrogen, can be successively separated from the possible by-products formed during the reaction with phosgene. Phosgene to use is commercially available already dissolved in appropriate solvents.

Alternatively, the derivative of formula (XV) can undergo reactions according to the following general scheme which allows preparation of symmetric and asymmetric carbonates, in detail:

both for the intermediates preparation (alcoholate and imidazolide) and for the end carbonate product, an inert solvent is chosen, i.e. chloroform, dichloro-methane, tetrahydrofuran:

alcoholate preparation is carried out on the selected alcohol using as base NaH or matallic Na either in catalytic or stoichiometric amounts, temperature can be between 0° C. and 60° C. (optimal room temperature), while reaction time ranges between 30 min to 12 hours (optimal 1 hour);

→the synthesis of the imidazolide of the second alcohol is carried out using as reagent carbonyl-diimidazole with temperature between 0° C. and 60° C. (optimal, room temperature), while reaction time ranges between 30 min to 12 hours (optimal 1 hour);.

→the synthesis of the end carbonates products is carried out by mixing properly the solutions of the alcoholate and of the imidazolide for a time of 6 to 24 hours (optimal 12 hours) at a temperature between 0° C. and 60° C. (optimal, room temperature).

Merely as an example, not limiting the present invention, a general method for the synthesis of derivatives of formula (I), is hereafter described:

EXAMPLE 3

A 50 mL solution of 3-(2-(hydroxymethyl)phenyl)-5-(3-ethoxyphenyl)-1H-1,2,4 triazole (3 g, 10 mmoles) in tetrahydrofuran, at room temperature, is added an 80% NaH suspension (310 mg, 10 mmoles) in tetrahydrofuran (50 mL). The reaction mixture is shacked at room temperature for 1 hour. The resulting solution is then added to a tetrahydrofuran solution containing the imidazolide of the selected alcohol obtained by reacting the alcoholic derivative (10 mmoles) with 1,1'-carbonyl-diimidazole (1.65 g, 10 mmoles) in tetrahydrofuran (20 mL) for 1 hour at room temperature. The mixture is stirred at room temperature for 12 hours, then solvent is take to dryness under vacuum and the residue re-dissolved in methylene chloride. The organic phase is washed with water, dried by anhydrous $Na_2SO_4$ and evaporated under vacuum. The obtained crude material is purified by column chromatography on silica gel (eluent hexane-ethylacetate, 8:2, v/v). After evaporation of the solvents, the solid pure product obtained is re-dissolved in hexane, filtered and dried under vacuum.

The compounds described below were prepared according to the procedure reported in Example 3.

EXAMPLE 4

Preparation of 3-(2-(ethoxy-carbonyloxymethyl) phenyl-5-(3-ethoxyphenyl)-1H-1,2,4-triazole Yield 52%; melting point =124–126° C.

$^1$H-NMR: 7.98 (1H, t, J=4.1 Hz); 7.72–7.74 (6H, m); 7.06 (1H,d, J=6.9 Hz); 5.68 (2H, s); 4.16 (2H, q, J=7.0 Hz), 4.14 (2H, q, J=7.1 Hz); 1.40 (3H, t, J=7.0 Hz); 1.21 (3H, t, J=7.1 Hz).

$^{13}$C-NMR: 158.76, 154.21, 133.65, 129.83, 129.04, 128.77, 128.60 (2C), 118.16 (2C), 115.86, 112.04 (2C), 67.20, 63.33, 63.15, 14.36, 13.82.

EXAMPLE 5

Preparation of 3-(2-(butoxy-carbonyloxymethyl) phenyl-5-(3-ethoxyphenyl)-1H-1,2,4-triazole Yield 58%; melting point=119–121° C.

$^1$H-NMR: 8.00 (1H, t, J=4.8 Hz); 7.70–7.40 (6H, m); 7.03 (1H,d, J=7.2 Hz); 5.62 (2H, s); 4.12 (2H, q, J=7.0 Hz), 4.03 (2H, t, J=6.4 Hz); 1.49 (2H, m) ; 1.36 (3H, t, J=7.0 Hz); 1.23 (2H, m); 0.80 (3H, t, J=7.3 Hz).

$^{13}$C-NMR: 158.70, 154.29, 133.51, 129.89, 129.20 (2C), 128.63 (2C), 128.35 (2C) , 118.15 (2C), 115.96, 111.98 (2C), 67.27, 67.17, 63.20, 18.03,14.26, 12.98.

EXAMPLE 6

Preparation of 3-(2-(hexyloxy-carbonyloxymethyl) phenyl-5-(3-ethoxyphenyl)-1H-1,2,4-triazole Yield 42%; melting point =90–92° C.

$^1$H-NMR: 8.07 (1H, m); 7.69–7.40 (6H, m); 7.06 (1H, d, J=7.3 Hz); 5.68 (2H, s); 4.15 (2H, q, J=7.0 Hz), 4.07 (2H, t, J=6.6 Hz); 1.56 (2H, m); 1.40 (3H, t, J=7.0 Hz); 1.23 (6H, m); 0.85 (3H, t, J=6.5 Hz).

$^{13}$C-NMR: 158.76, 154.29, 133.65, 129.79, 128.87 (2C), 128.59 (2C), 128.15 (2C), 118.15 (2C), 115.87, 112.03 (2C), 67.37, 67.29, 63.13, 30.49, 27.87, 24.52, 21.61,14.36, 13.43.

EXAMPLE 7

Preparation of 3-(2-(octyloxy-carbonyloxymethyl) phenyl-5-(3-ethoxyphenyl)-1H-1,2,4-triazole Yield 49%; melting point=86–89° C.

$^1$H-NMR: 8.06 (1H, m); 7.72–7.40 (6H, m7); 7.05 (1H, d, J=7.1 Hz); 5.69 (2H, s); 4.15 (2H, q, J=7.0 Hz), 4.07 (2H, t, J=6.4 Hz); 1.56 (2H, m); 1.40 (3H, t, J=7.0 Hz); 1.23 (10H, m); 0.86 (3H, t, J=6.5 Hz).

$^{13}$C-NMR: 158.76, 154.28, 133.65, 129.77, 129.01, 128.84, 128.59 (2C), 128.59 (2C), 128.13 (2C), 118.16 (2C), 115.83, 112.03 (2C), 67.37, 67.30, 63.13, 30.88, 27.91, 24.89, 21.72,14.35, 13.53.

In the following example 6, the synthesis of one derivative of formula (I), where the group $R_7$ is chosen of formula (XII), symmetric carbonates, is described:

EXAMPLE 8

Preparation of Di-(2-(5-(3-ethoxyphenyl)-1H-1,2,4-triazol-3-yl) phenylmethyl) carbonate A 15 mL solution of 3-(2-(hydroxymethyl)phenyl)-5-(3-ethoxyphenyl)-1H-1,2,4 triazole (0.7 g, 2.4 mmoles) in tetrahydrofuran, at room temperature, is added a 80% NaH suspension (35 mg, 1.2 mmoles) in tetrahydrofuran (15 mL). The reaction mixture is shacked at room temperature for 1 hour. The resulting solution is then added 1,1'-carbonyl-diimidazole (192 mg, 1.2 mmoles) in tetrahydrofuran (20 mL) for 1 hour at room temperature. The mixture is stirred at room temperature for 12 hours. Solvent is taken to dryness under vacuum and the residue re-dissolved in methylene chloride. The organic phase is washed with water, dried by anhydrous Na$_2$ SO$_4$ and evaporated under vacuum. The obtained crude material is purified by column chromatography on silica gel (eluent hexane-ethylacetate, 7:3, v/v). After evaporation of the solvents, the solid pure product obtained is re-dissolved in hexane, filtered and dried under vacuum. 212 mg of the compound (XVII) were obtained.

Yield 36%; melting point =143–145° C.

$^1$H-NMR: 8.07 (2H, m), 7.69–7.38 (12H, m); 7.03 (2H,d, J=8.4 Hz); 5.72 (4H, s); 4.12 (4H, q, J=7.0 Hz), 1.37 (6H, t, J=7.0 Hz);.

$^{13}$C-NMR: 158.74, 154.21, 133.59, 129.81 (2C), 128.97 (2C), 128.02 (2C), 118.18 (2C), 115.88, 112.00 (2C), 67.41, 63.13, 14.33.

EXAMPLE 9

(a) 2-BENZOYLOXYMETHYL BENZOIC ACID

Phtalide (50 g, o.37 moles) is dissolved in 20% NaOH (267 mL, 1.33 moles) by eating the mixture at 60° C. The resulting solution is diluted with water-ice (2.2 kg) and added, for 10 min under vigorous stirring, with benzoyl chloride (56 mL, 0.48 moles). After 1 hour the reaction mixture is dissolved with 4 L water, the pH adjusted to 2.5 by 10% HCl and the precipitate is filtered under vacuum. The solid is suspended into 600 mL of heat water (50° C.), shacked for 5–10 min and re-filtered. The procedure is repeated four times. The crude compound is crystallised from ethanol/water 7:3 (200 mL).

Yield: 45 g

TLC: toluene:ethyl acetate: acetic acid, 5:5:0.1

(b) 2-BENZOYL-OXYMETHYL-BENZOIC ACID CHLORIDE

To the solution of the 2-benzoyloxymethyl benzoic acid (40 g, 0.15 moles) in chloroform (400 mL), anhydrous pyridine (0.92 mL, 4 mmoles) is added under stirring and thereafter, within 10 min, thionyl chloride (13.7 mL, 0.18 moles). The reaction mixture is refluxed for 1 hour then is take to dryness. The residue is re-dissolved in chloroform and re-dried. The operation is repeated another two times and the chloride obtained used (c) 2-BENZOYL-OXYMETHYL-BENZOIC ACID HYDRAZIDE To the solution of 98% hydrazine hydrate (24 mL, 0.62 moles), in 95% ethanol (120 mL) cooled into an ice bath, absolution of the 2-benzoyloxymethyl benzoic acid chloride (0.15 moles)in methylene chloride (120 mL), is added drop wise. The reaction mixture is stirred at room temperature for 2 hours, the lower phase is separated, and the upper phase is re-extracted by methylene chloride. The organic phases are poured and washed with NaCl saturated water and take to dryness.

The residue is shelled into ethyl ether (500 mL), filtered and dried.

Yield: 36.5

TLC: toluene:ethyl acetate: acetic acid, 5:5:0.1

(d) 3-ETHOXY- ETHYL-BENZIMIDATE

To a mixture of 3-ethoxy benzonitrile (25 mL, 0.177 moles) and absolute ethanol (12.3 mL, 0.2 moles) cooled into an ice-bath, HCL gas is bubbled until saturation. After standing in refrigerator for 48 hour (the yield is increased by prolonging the standing period) the crude material is suspended in ethyl ether, filtered and dried.

Yield: 18 g

The ethoxy ethyl benzimidate chloride obtained is dissolved in water and alkalinised by 5% $NaHCO_3$. By extraction with 1,1,3 trichloro-ethane (200 mL) the ethoxy ethyl benzimidate base is obtained. The solution is dried to be used in the next step.

(e) 3-(2-BENZOYL-OXYMETHYL-PHENYL)-5-(O-ETHOXY-PHENYL)-1H-1,2,4 TRIAZOLE.

To the ethoxy ethyl benzimidate (base) solution (0.078 moles) in 1,1,3-trichloroethane from the previous step, the hydrazide of 2-benzoyl-oxymethyl-benzoic acid (19.2 g, 0.071 moles) is added. The mixture is heated first at 90° C. for 90 min then at 110+C. for 1 hour, trichloroethane is distilled under vacuum until precipitation starts. Xilene (250 mL) is added and the solution is heated under reflux by eliminating the reaction water with Marcusson. After 1 hour the reaction mixture is cooled to room temperature, the precipitate filtered and dried under vacuum.

Yield: 20 g

TLC: toluene:ethyl acetate: acetic acid, 5:5:0.1

(f) 3-(2-HYDROXY-METHYLPHENYL)-5-(ETHOXYPHENYL)-1H, 1,2,4-TRIAZOLE

A solution of 3-(2-benzoyl.oxymethylphenyl)-5-(O-ethoxyphenyl)-1H, 1,2,4 triazole (20 g, 0,05 moles) in 10% NaOH (86 mL) and 95% ethanol (130 mL) is warmed for 1 hour at 70° C .Ethanol is then evaporated under vacuum and the aqueous solution left, diluted with water (130 ml) and cooled by a ice-bath, is adjusted to pH 8 with 10% HCl. The obtained suspension is stirred at room temperature for some hours, the solid is filtered, dried under vacuum and finally crystallised from ethanol (100 mL).

Yield: 11.8 g

When R is chosen equal to —CO $R_8$, where $R_8$ is a saturated or a non saturated $C_1$–$C_{10}$ aliphatic hydrocarbon, the hydroxy group of derivative (XV), will be protected according to known methods. Protected derivative (XVb) will be also obtained and acylated according to known methods in order to introduce the —$COR_8$ group. Subsequently this acylated derivative will be de-protected and allowed to react with phosgene as reported above. In the case of X=Y=N, the acylation reaction could be carried out as described by EP80053. When $R_5$ is chosen:

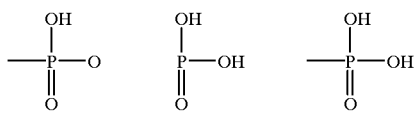

Derivatives of formula (I) are advantageously prepared starting from derivatives of formula (XV) (eventually submitted to a previous acylation reaction as already described) by reaction with phosphoric acid or equivalents according to known methods.

For derivatives of formula (I), when X=Y=N following the acylation procedure described above, both single compounds, where the substituent R is located on one of. the two adjacent nitrogen atoms and mixtures of the two possible isomers can be obtained.

In this latter case, the mixture can be separated into he single components by chemico-physical known methods. For example, the way a mixture can be resolved into the single components is a fractionated crystallisation, which take advantage of the different solubility of each compound in various solvents at different temperatures. Suitable solvents that can be used for this method are chosen as an example, among hexane, ethyl-acetate, $C_1$–$C_4$ alkyl ethers, methylen chloride, light petroleum ether and mixtures thereof. A further illustrative example of a method useful for the separation of the isomers' mixture is based on column chromatography, performed on non-acid, buffered adsorbents, as silica-gel buffered to pH=7. Another example of a method useful for the separation of the isomer mixture is based on the use of preparative high pressure liquid chromatography (PHPLC), carried out on proper columns, for example filled with silica-gel esterified with octyl-silane or octyl-decylsilane. Other obvious procedures useful for resolving a mixture of isomers into the single components are intended to fall within the scopes of the invention.

As reported in the literature, see Potts K. T , J: Chem. Soc. 3451, (1954) and Potts K. T., Chem. Rew. 61, 99 (1961), Kubota and Uda, Chem. Pharm. Bull. 23(5), 955 (1975), due to the high mobility of the hydrogen atoms of 1,2,4-triazoles, compounds of formula (I) of the present invention where X=Y=N, are to be regarded as a mixture of two tautomeric forms, i.e. those in which the hydrogen atom is located on one or the other of the two adjacent nitrogen atoms of the triazole ring.

Depending on the nature of the substitutes at the 3 and 5 positions, a form may predominate on the other one. Consequently, both mentioned tautomeric forms must be considered as part of the present invention. It is known that tautomeric forms rapidly exchange in between and consequently behave as a dynamic equilibrium. Anyway, throughout the whole description and claims relative to the present invention, 3,5 diphenyl-1H-1,2,4-triazoles according to the present invention, will be numbered as reported in the compounds described throughout the text.

The derivatives of general formula (IV) can be advantageously prepared as reported, for example, by GB 1479759 and GB 1484615.

It has been shown that the compounds of the present invention, do not retain hormonal or anti-hormonal or lympholytic activity; differently from the alkylating agents they inhibit the antibody formation versus corpuscular antigens (ram erythrocytes) when administered after the antigen; differently from anti-metabolites they are inactive in all the tumour models tested (leukemia P-388, L1210, EL(4) T, and the lymphoma 70(Z)B) made exception for the choriocarcinoma; Differently from cyclosporin A, they do not exert a selective action on lymphocytes B and/or T. At last, the compounds of the present invention do not interfere with the macrophagic function and do not retain cytotoxic activity neither in in vivo or in vitro experimental models.

As already described, the derivatives of general chemical formula (I) and (IV) were shown effective in animal models predictive for anti-psoriasis and anti-ulcerous cholitis activity, whereas clinical studies did showed their effectiveness in the treatment of dermatological diseases as the psoriasis and atopic dermatitis.

Apropos, in an animal model predictive for the evaluation of an anti-psoriasis activity as reported by Lowe M.L., Drug Dev. Res. 13/2–3, 147–155 (1988), Gallado Torres H. I. et al., Phatobiology 63/6, 341–347 (1995), compounds of formula V, VI, VII, VIII, IX, X, XI, XII, XIII and XIV have been tested in mice where a chronic hyper-proliferative dermatitis, characterised by epidermic hyperplasia, was induced.

The results obtained show the high efficacy of the selected compounds in inhibiting differentiation and/or proliferation of degenerated epithelial cells. Inhibition. of DNA synthesis of the epidermis of hairless mice 16 hours after the epicutaneuos treatment with compounds V and XIV.

The compounds were administered dissolved and/or suspended in sesame oil at the concentration of 0.25%.

| COMPOUND | DNA 10% concentraton in tissue ± S.D. |
|---|---|
| Vehicle | 115.2 ± 9.30 |
| V | 32.3 ± 6.4 |
| VI | 55.8 ± 9.2 |
| VII | 44.3 L 6.6 |
| VIII | 39.1 ± 5.7 |
| IX | 46.3 L 7.3 |
| X | 68.6 ± 9.4 |
| XI | 72.4 ± 10.1 |
| XII | 26.7 ± 4.5 |
| XIII | 48.3 ± 5.9 |
| XIV | 75.8 ± 8.8 |

Because of these results, the therapeutic activity of compound of formula XIII in the therapy of psoriasis, was evaluated as. reported in the Example 10, as follows:

EXAMPLE 10

In some patients observed individually and thereafter by a controlled study, the anti-psoriasis activity was evaluated according to an unbalanced, double-blind experimental design.

In detail, 18 male patients, aged more than 18 years, demonstrating at the physical examination and from the routine laboratory (haematology, blood chemistry, urinalysis) a general good health condition, having a severe chronic pathology characterised by large-plaques of psoriasis vulgaris involving an area between 10–20% of the whole body surface, previously unsuccessfully treated (at least 3 months before) with topical and systemic known therapies, have been enrolled and randomised in two-groups of 6 (control) and 12 (treated) units.

The treated group received compound XIII formulated as cream for topical use at the concentration of 0.1% (1 mg/g) once daily for 7 consecutive days, whereas the control group received, according to the same dose regime, placebo only.

The $8^{th}$ day, on three different lesions from different areas, an efficacy judgement, based on a semi-quantitative evaluation criteria of the erythema, was given by the dermatologist: 0=absent, 1=minimum, 2=moderate, 3=severe. These measures were then summarised in a global comparative evaluation: −1(worsening), 0=(no or minimum (10%) improvement), +1=(moderate improvement, 11 to 50%), +2=(marked improvement, 51 to 99%) and +3 =complete recovery.

TABLE 1

VALUTATION OF CLINICAL EFFICAY IN COMPOUND (XIII) (0.1% cream) IN PATIENTS AFFECTED BY VULGARIS PSORIARIS TREATED BY EPICUTANEOUSLY 1 x DIE x 7 CONSEQUTIVE DAYS

| CLINICAL RESPONSE | PLACEBO (N = 6) | COMPOUND (XIII) (N = 12) |
|---|---|---|
| worsening | 2 | 0 |
| none or minimum | 4 | 0 |
| moderate improvement | 0 | 3 |
| marketed improvement | 0 | 7 |
| recovery | 0 | 2 |

All patients of the two experimental groups completed the study without the treatment give rise to untoward local and/or systemic effects. The laboratory examinations, repeated within 7 days after the study end, did not show changes of clinical relevance of any of the parameters assayed.

Dealing with the activity of the compounds object of the present invention, on the inflammatory diseases of the low intestine, some compounds, namely V, VI, X and XI, were tested in animal models of ulcerous cholitis (Wallace J. L. et al., Eur. J. Pharmacol. 257, 249 (1994); Renter B. K. et al. J. Clin. Invest. 98, 2076–2085 (1996).

In particular, compound VI, when administered daily by oral route to Wistar rats, dissolved in sesame oil at the concentration of 2 mg/mL, at the dose of 1 mg/kg, did show a good activity in favouring colon ulcers repair, in re-establishing the normal thickness of the intestinal wall and in decreasing the granulocytes infiltration proper of an inflammatory condition.

Studies of acute and sub-acute toxicity were carried out on compound XIII, the results are herewith reported. The studies, carried out in different rodent and non rodent animal species, showed that at the effective doses, the therapeutic index is extremely favourable.

TABLE 2

ACUTE TOXICITY VALUES IN MICES, RATS AND HAMSTER TREATED BY PARENTERAL ROUTE

| ANIMAL SPECIES | ADMINISTRATION ROUTE | DL 50 (mg/kg) |
|---|---|---|
| Mice | subcutaneous | 3910 |
| S.D. Rats | subcutaneous | 3190 |
| S.D. Rats | intramuscolar | >2000 |
| Sirian hamster | subcutaneous | >2000 |
| recovery | 0 | 2 |

In S.D. rats administered daily for 20 consecutive days by subcutaneous route doses of 3, 6 and 10 mg/kg no toxic effects were observed on hepatic, hematopoietic and renal functions. A mild and transient effect on the body weight increase, was recorded at the higher dose. similarly, the hepatic, hematopoietic and renal functions were not altered in cynomolgus monkeys and in baboons given daily for 5 consecutive days by intramuscular route doses up to 7.5 mg/kg.

Mutagenicity studies carried out in vitro and in vivo: the Ames test performed in strains of Salmonella typhimurium (up to 5 mg/mL), the chromosome aberration test performed in lung cells of Chinese hamster (up to $10^{-7}$ M), the micronucleous test performed in bone marrow cells of mouse (up to 600 mg/kg, s.c.) did show for compound XIII, complete lack of mutagenic potential. Studies of general pharmacology, carried out in Beagle dogs, did not show effects on the cardiovascular system up to a daily intramuscular dose of 4 mg/kg given for 15 consecutive days.

Compound XIII, administered intramuscularly to. S.D. rats at the daily dose of 40 mg/kg for 5 consecutive days, induced a slight decrease of the spontaneous motor activity, of curiosity and of the muscular tone. Taking into account that in the therapy of psoriasis, at the active doses (cream 0.05–0.1%, i.e. 0.5–1 mg/g) the maximum applicable amount by epicutaneous route (whole body surface) as cream formulation is of about 50 g, i.e. 25–50 mg, and that the percutaneous absorption is about 10% of the applied dose, the maximum systemically bioavailable dose should be lower than 0.05–0.1 mg/kg.

These data confer to the product, when administered according to the therapeutic regimens studied (1/die for 7 consecutive days), a high safety of use.

Nitrogen heterocyclic aromatic derivatives of formula I and IV, when used according to the present invention, are advantageously prepared, as active principles, in pharmaceutical formulations for topical use, so to be administered, for example, by epicutaneous, oral and rectal route.

In the event of dermatological diseases derivatives object of the present invention, can also be advantageously prepared in pharmaceutical formulations suitable for transdermic application.

Mentioned pharmacutical preparations are properly formulated by employing, for example, proper transdermic release systems, particularly useful for the epicutaneous dosing, or are formulated in lipid vehicles (creams or ointments).

For example, as vehicles for the epicutaneous administration, can be advantageously used oils of vegetable origin or esters of fatty acids as sesame oil, maize seeds oil, corn oil, peanut oil, cotton seed oil, and ethyl oleate.

Other oily vehicles may as well be used provided that they are safe in the volume administered and do not interfere with the therapeutic efficacy of the preparation. As known to the art skilled man, these preparations may also contain antimicrobial agents, to prevent growth of micro-organisms in the preparation, and antioxidants, essentially to prevent the development of rancidity of the oily vehicle.

Always as example, the optimal dose contains, on the average, from 0.01 to 0.5% (w/w) of at least one derivative of the present invention of formula I and IV, as active principle, moreover for each product the optimal dose depends on the application area of the patient to be administered.

Is hereafter reported as example 11 a type formulation, referring to a cream useful for the treatment of psoriasis according to the present invention, which contains compound XIII as active principle.

EXAMPLE 11

100 mg of cream containing:

| | |
|---|---|
| Compound (XIII) | 100.0 mg |
| Crodabase PC-M | 10.24 g |
| Cetylic Alcohol | 5.37 g |
| liquid semi-synthetic tryglicerides | 8.51 g |
| dymeticone | 1.70 g |
| paraseptics | 0.15 g |

| | |
|---|---|
| sweet almond oil | 2.80 g |
| stearine (stearic acid) | 0.97 g |
| propylen glycol | 4.26 g |
| tetra-sodic EDTA | 0.14 g |
| carbomer (carboxy-vinylpolymer) | 0.16 g |
| triethanolamine 99% | 0.10 g |
| depurated water (to 100 g) | 65.5 g |

Crodabase PC-M is a product of Croda Company whose claimed composition is as follows: C 8-18 Acid POE, 3 C 6-22 alcohol ester and 0 6-22 alcohol.

Dealing with the oral administration in the therapy of ulcerous cholitis, are advantageously used gastro-protected controlled-release capsules (pH dedendent) containing lyposom preparations and/or lipids entrapping the active principle, which warrant the release at the site of action (colon).

Analogously, for the rectal administration, the use of foams containing lipid bases and appropriate surfactants can be useful in the treatment of the diseases of the low intestine.

EXAMPLE 12

Brief description of controlled release systems. Gastro-protected capsules, pH dependent, containing a powder of lyophilised pre-lyposoms.

| COMPOUND | RELATIVE AMOUNTS |
|---|---|
| Active principle | 25 mg |
| Cholesterol | 10 mg–50 mg |
| Phospholipids* | 30 mg–150 mg |

*= Phospholipids hydrogenated by soia oil

What is claimed is:

1. A method for the topical treatment of epithelial tissue diseases which comprises administering to a subject in need thereof an effective amount of an heterocyclic aromatic compound having the following formulae (I) or (IV):

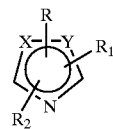

(I)

wherein:
X=Y=N;
R is selected from
  hydrogen;
  COR$_8$ wherein R$_8$ is C$_1$–C$_{10}$ alkyl, C$_2$–C$_4$ alkenyl, C$_2$–C$_4$ alkinyl, phenyl optionally substituted by 1 to 3 substituents, benzyl, C$_1$–C$_4$ alkylamino, di-(C$_1$–C$_4$ alkyl)amino, phenylamino optionally substituted by 1 to 3 substituents, C$_1$–C$_4$ haloalkyl, C$_1$–C$_4$ alkoxy, benzyloxy, each optional substituent being independently selected from halogen, C$_1$–C$_4$ alkyl, C$_1$–C$_4$ alkoxy, trifluoro-methyl, CN, nitro, amino, di-(C$_1$–C$_4$ -alkyl)amino, acyl-aminoC$_2$–C$_4$ and methylenedioxy; and
  SO$_2$R$_{12}$ wherein R$_{12}$ is selected from C$_1$–C$_4$ alkyl, phenyl, (C$_1$–C$_4$ alkyl)phenyl, (C$_1$–C$_4$ alkoxy)phenyl, and acetyl-phenyl;

$R_1$ has the following formula:

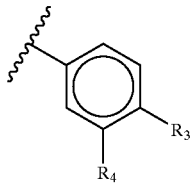 (II)

wherein $R_3$ and $R_4$ are independently selected from:
  hydrogen;
  halogen;
  $C_1-C_{10}$ alkyl or alkoxyl $C_1-C_{10}$;
  allyloxy, propargyloxy;
  trifluoro-methyl;
  phenyl; and
  di-methylamino, or $R_3$ and $R_4$ together form a methylenedioxy group;

$R_2$ has the following structure:

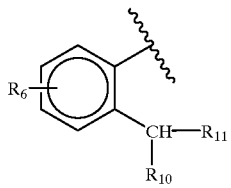 (III)

wherein $R_6$ is selected from:
  hydrogen,
  halogen,
  $C_1-C_{10}$ alkyl and alkoxyl $C_1-C_{10}$;

$R_{10}$ is selected from:
  hydrogen; and
  methyl;

$R_{11}$ is selected from:
  hydrogen;
  $C_1-C_4$ alkyl; and
  formyl;
  $OR_5$ wherein $R_5$ is selected from hydrogen, and $C_1-C_4$ alkyl, or $R_5$ is selected from:

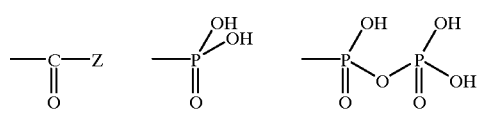

wherein Z=OR, with $R_7$ is a saturated or non-saturated, linear or branched $C_1-C_{20}$ aliphatic hydrocarbon, or $R_7$ has the following formula:

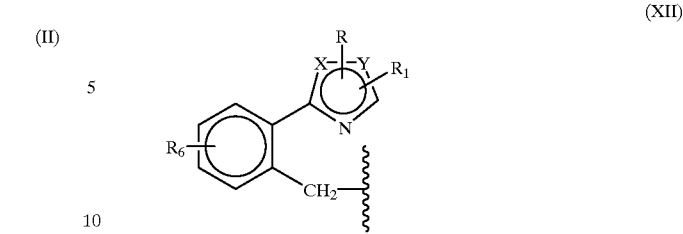 (XII)

wherein R, $R_6$, $R_1$, X and Y are defined as above or Z is selected from $C_1-C_{20}$ linear or branched alkyl, $C_2-C_4$ alkenyl, $C_2-C_4$ alkinyl, phenyl optionally substituted by 1 to 3 substituents, benzyl, $C_1-C_4$ alkylamino, di-($C_1-C_4$ alkyl)amino, phenyl-amino optionally substituted by 1 to 3 substituents, $C_1-C_4$ halo-alkyl, $C_1-C_4$ alkoxy, benzyloxy, each optional substituent being independently selected from halogen, $C_1-C_4$ alkyl, $C_1-C_4$ alkoxy, trifluoromethyl, CN, nitro, amino, of ($C_1-C_4$ alkyl)amino, acyl-amino$C_2-C_4$ and methylenedioxy;

or Z is $NHR_9$ wherein $R_9$ is an alkenyl chain $C_1-C_{20}$, linear or branched;

provided that $R_1$ and $R_2$ are not located on two adjacent atoms of the heterocyclic aromatic ring; Formula (IV):

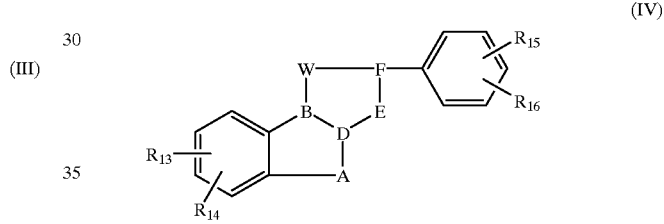 (IV)

wherein
  $R_{15}$ and $R_{16}$ are selected from:
    hydrogen;
    halogen;
    $C_1-C_4$ alkyl or alkoxyl $C_1-C_4$;
    $C_3-C_5$ alkyl or alkoxyl $C_1-C_5$;
    cycloalkyloxyl $C_3-C_6$,
    benzyloxy; and
    halogen;
or
  $R_{15}$ and $R_{16}$ represent together a methylenedioxy group;
  $R_{13}$ $R_{14}$ are selected from:
    hydrogen;
    halogen; and
    $C_1-C_4$ alkoxyl;
  A is —$CH_2$—CH=CH—, —$CH_2CH_2$—, $(CH_2)_3$, or —$CH_2S$—;
  B is C or N;
  D is C, or N;
  or B and D together are equal to C=C;
  E is N, C, CO, NH, CH, $NR_{17}$, or $CR_{17}$ wherein $R_{17}$ is a linear $C_1-C_4$ alkyl;
  F is CH, or N;
  W is selected from N, NH, CH, $NR_{17}$, $CR_{17}$, and $CR_{16}$, wherein $CR_{17}$ is defined as above and $R_{18}$ is carboxy, carbo($C_1-C_4$ alkyl), carbamyl, mono or di-($C_1-C_4$ alkyl)carbamyl, hydroxymethyl; provided that the ring formed by W-F-E-D-B is a triazole or a tetrazole.

2. The method according to claim 1 wherein, in formula (IV), $R_{13}$ and $R_{14}$ are both hydrogen; A is selected from —$CH_2$—, —CH=CH— and —$CH_2$—$CH_2$—; D is N; B is C; W is N, $R_{15}$ is hydrogen, and $R_{16}$ is $C_1$-$C_4$ alkoxy or phenyl.

3. The method according to claim 1 wherein the epithelial tissue diseases are psoriasis or atopic dermatitis.

4. The method according to claim 1 wherein the epithelial tissue diseases are ulcerative colitis or Crohn's disease.

5. The method according to claim 1 wherein the compound of formula (IV) has the following chemical structure:

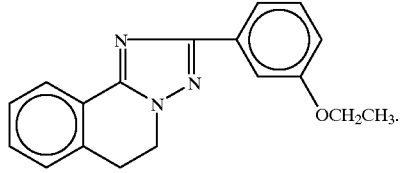
(X)

6. The method according to claim 1 wherein the compound of formula (IV) has the following chemical structure:

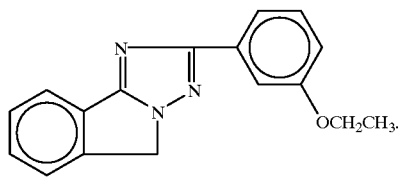
(XI)

7. The method according to claim 1 wherein the compound of formula (IV) has the following chemical structure:

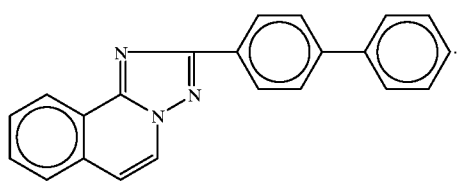
(XII)

8. The method according to claim 1 wherein the compound of formula (I) has the following chemical structure:

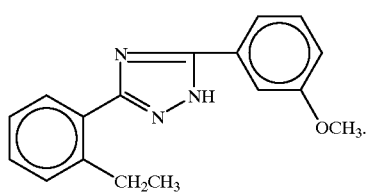
(XIII)

9. The method according to claim 1 wherein the compound of formula (I) has the following chemical structure:

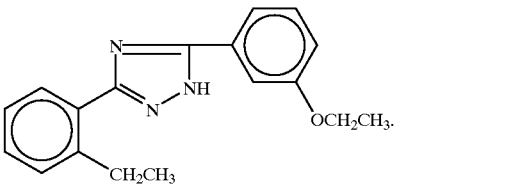
(V)

10. The method according to claim 1 wherein the compound of formula (I) has the following chemical structure:

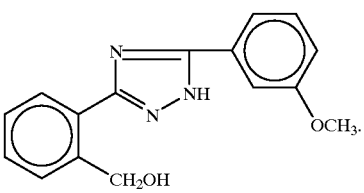
(VI)

11. The method according to claim 1 wherein the compound of formula (I) has the following chemical structure:

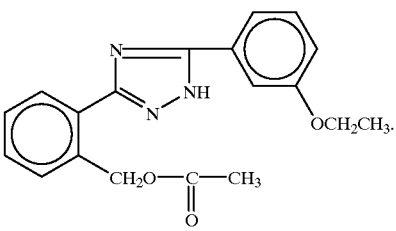
(VII)

12. The method according to claim 1 wherein the compound of formula (I) has the following chemical structure:

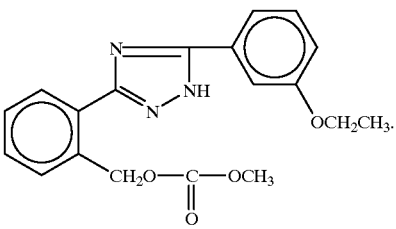
(VIII)

13. The method according to claim 1 wherein the compound of formula (I) has the following chemical structure:

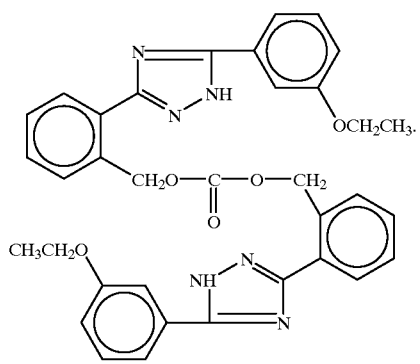

(IX)

14. The method according to claim 1 wherein the administration is by the epicutaneous route.

15. The method according to claim 1 wherein the administration is by the oral route.

16. The method according to claim 1 wherein the administration is by the rectal route.

17. The method according to claim 1 wherein the compound of formula (I) or (IV) is administered in combination with another drug to treat epithelial tissues.

18. A pharmaceutical topical, epicutaneous or transdermal composition which comprises together with a carrier or diluent a compound of claim 1 as active ingredient.

19. The pharmaceutical composition according to claim 18 formulated using lipid vehicles.

20. The pharmaceutical composition according to claim 19 wherein said lipid vehicles are selected from sesame oil, corn oil, peanut oil, cotton seed oil, and ethyl oleate.

21. The pharmaceutical composition according to claim 18 which further comprises an anti-microbial agent.

22. The pharmaceutical composition according to claim 18 which further comprises an anti-oxidant.

23. The pharmaceutical composition according to claim 18 which comprises 0.01% to 0.5% (w/w) of active ingredient.

24. The pharmaceutical composition according to claim 18 which is a cream containing in 100 g:

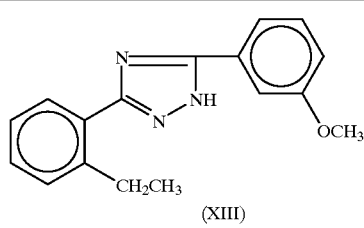

(XIII) 100.0 mg

| | |
|---|---|
| Crodabase PC-M | 10.24 g |
| Cetylic Alcohol | 5.37 g |
| semi-synthetic liquid triglycerides | 8.51 g |
| dymeticone | 1.70 g |
| paraseptics | 0.15 g |
| sweet almond oil | 2.80 g |
| stearine (stearic acid) | 0.97 g |
| propylene glycol | 4.26 g |
| tetra-sodic EDTA | 0.14 g |
| carbomer (carboxy-vinylpolymer) | 0.16 g |
| triethanolamine 99% | 0.10 g |
| purified water (to 100 g) | 65.5 g. |

25. A nitrogen heterocyclic aromatic compound having the following formula (I):

(I)

wherein $X=Y=N$;

R is selected from:
hydrogen; and
$COR_8$ wherein $R_8$ is a saturated or non-saturated $C_1$–$C_{10}$ aliphatic hydrocarbon;

$R_1$ has the following structure:

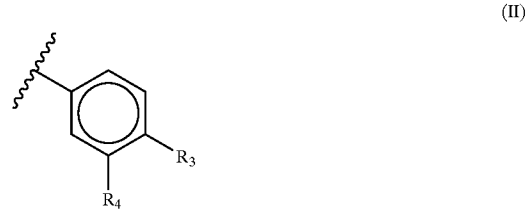

(II)

wherein:

$R_3$ and $R_4$ are each independently selected from hydrogen;
halogen;
$CC_1$–$C_{10}$ alkyl and alkoxyl $C_1$–$C_{10}$;
or $R_3$ and $R_4$ together form a methylenedioxy group;

$R_2$ has the following structure:

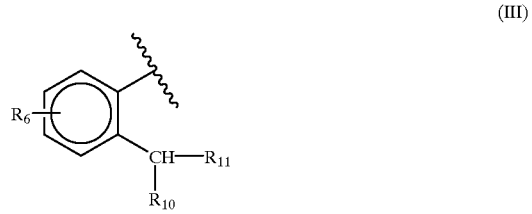

(III)

wherein $R_6$ is selected from:
hydrogen;
halogen;
$C_1$–$C_{10}$ alkyl and $C_1$–$C_{20}$ alkoxyl;

$R_{10}$ is hydrogen, $R_{11}$ is $OR_5$, wherein $R_5$ is selected from $C_1$–$C_{20}$ saturated or non-saturated, linear or branched aliphatic hydrocarbon, or $R_5$ is selected from:

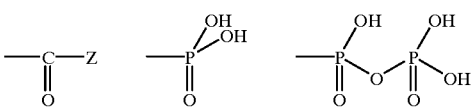

wherein $Z=OR$, with $R_7$ selected from a saturated or non-saturated, linear or branched $C_1$–$C_{20}$ aliphatic hydrocarbon, or $R_7$ has the following formula (XII):

(XII)

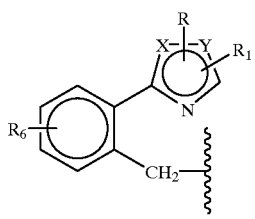

wherein R, $R_1$, $R_6$, X and Y are defined as above or Z is NHR, wherein $R_9$ is a $C_1$–$C_{20}$ linear or branched alkyl chain;

provided that $R_1$ and $R_2$ are not located on two adjacent atoms of the heterocyclic aromatic ring.

26. The nitrogen heterocyclic aromatic compound according to claim 25 having the following formula:

(VIII)

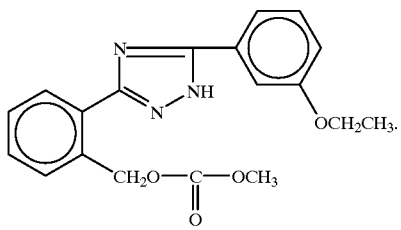

27. The nitrogen heterocyclic aromatic compound according to claim 25 having the following formula:

(IX)

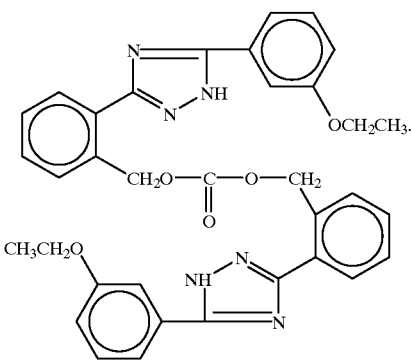

28. A pharmaceutical composition which comprises together with a carrier or a diluent a compound of claim 25 as active ingredient.

29. A pharmaceutical composition according to claim 28 for the topical treatment of psoriasis, atopic dermatitis, ulcerative colitis or Crohn's disease.

* * * * *